(12) United States Patent
Espina Perez et al.

(10) Patent No.: US 8,312,174 B2
(45) Date of Patent: Nov. 13, 2012

(54) PROTOCOL CONVERTER FOR WIRELESS PATIENT MONITORING

(75) Inventors: Javier Espina Perez, Aachen (DE); Thomas Falck, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 462 days.

(21) Appl. No.: 12/522,395

(22) PCT Filed: Jan. 8, 2008

(86) PCT No.: PCT/IB2008/050039
§ 371 (c)(1),
(2), (4) Date: Jul. 8, 2009

(87) PCT Pub. No.: WO2008/084434
PCT Pub. Date: Jul. 17, 2008

(65) Prior Publication Data
US 2010/0049005 A1   Feb. 25, 2010

(30) Foreign Application Priority Data
Jan. 11, 2007   (EP) .................................... 07100362

(51) Int. Cl.
*G06F 15/16*   (2006.01)
(52) U.S. Cl. .................. 709/250; 709/230; 709/466
(58) Field of Classification Search .................. 709/250
See application file for complete search history.

(56) References Cited

U.S. PATENT DOCUMENTS

| | | | |
|---|---|---|---|
| 5,497,373 A * | 3/1996 | Hulen et al. .................. 370/259 |
| 5,870,626 A * | 2/1999 | Lebeau ........................ 710/11 |
| 5,881,105 A * | 3/1999 | Balachandran et al. ...... 375/259 |
| 6,937,323 B2 * | 8/2005 | Worthington et al. .......... 356/73 |
| 7,321,599 B1 | 1/2008 | Yen et al. |
| 2002/0091843 A1 | 7/2002 | Vaid |
| 2002/0173704 A1 | 11/2002 | Schulze et al. |

(Continued)

FOREIGN PATENT DOCUMENTS
WO   03049592 A2   6/2003
(Continued)

OTHER PUBLICATIONS
Industrial Rated Wireless Serial RS232 RS485 to Ethernet Converter http://www.datalilnkcom.net/industrial_ethernet/dl-esr90lwb.htm.
(Continued)

*Primary Examiner* — Hua Fan (57) ABSTRACT

The invention relates to a wireless device for medical data transmission that comprises a wireless interface, a processor, and a medical equipment interface arranged to provide connection to an item of medical equipment. The processor is arranged to communicate with the medical equipment interface and the wireless interface, and is also 5 arranged to perform a protocol adaptation. The protocol adaptation takes place from a protocol of incoming data received at the medical equipment interface to a protocol of data to be transmitted through the wireless interface, or vice versa. The protocol adaptation comprises individual or combined filtering, gathering, partitioning, prioritizing, or discarding the incoming data. The processor is further arranged to read a configuration file containing an 10 adaptation specification that pertains to the protocol adaptation; and to perform the protocol adaptation in compliance with the adaptation specification. The invention also relates to a method for setting up the wireless device.

5 Claims, 2 Drawing Sheets

U.S. PATENT DOCUMENTS

| | | | |
|---|---|---|---|
| 2003/0040881 A1 | | 2/2003 | Steger et al. |
| 2004/0127802 A1 | | 7/2004 | Istvan et al. |
| 2005/0102167 A1 | | 5/2005 | Kapoor |
| 2005/0203350 A1 | | 9/2005 | Beck |
| 2006/0122466 A1 | | 6/2006 | Nguyen-Dobinsky et al. |
| 2007/0283030 A1 | * | 12/2007 | Deininger et al. ............ 709/230 |
| 2009/0058635 A1 | * | 3/2009 | LaLonde et al. ......... 340/539.11 |

FOREIGN PATENT DOCUMENTS

| | | |
|---|---|---|
| WO | 2006114155 A1 | 11/2006 |
| WO | 2007058798 A2 | 5/2007 |

OTHER PUBLICATIONS

MaxStream XBee PRO PKG RF Modem http://www.microdaq.com/maxstream/zigbee/fr_modem.php.

Standalone Wireless RF Radio Modem http://www.datalinkcom.net/wireless_radio_modems/xstream_pkg_ra.html.

Baisa, N.; Designing Wireless interfaces for patient monitoring equipment; 2005; Medical Electronics; pp. 46-50.

Shnayder, V., et al.; Sensor Networks for Medical Care; 2005; Tech. Report TR-08-05, Division of Engineering and Applied Sciences—Harvard University; pp. 1-14.

* cited by examiner

PROTOCOL CONVERTER FOR WIRELESS PATIENT MONITORING

FIELD OF THE INVENTION

The invention pertains to a wireless device for transmission of medical data from and/or to an item of medical equipment.

BACKGROUND OF THE INVENTION

Monitoring of vital signs is an essential element in intensive care units and other hospital departments. Medical sensors-like Pulse Oximeter (SpO2) or Non-Invasive Blood Pressure (NIBP)—are currently wired to bedside monitors, which analyze, interpret and visualize the patient's waveforms, numeric values and alarms. This set-up ties patients to their beds, which is inconvenient for them and complicates work for caregivers. It makes therefore sense to develop wireless monitoring systems. For cost reasons, these new systems will not be built from scratch but rather based on preceding systems by replacing the wired links by wireless links.

In order to turn a wired link (serial line) into a wireless link, the sender (e.g. the medical measurement sensor) and the receiver (e.g. the patient monitor to which the sensor is connected) need to be provided with a radio module each. The wireless link between the radio modules of sender and receiver replaces the original wired connection. Nevertheless the original wire-based protocol may not be suitable for wireless transmission because:

The bandwidth it uses is excessive for the wireless technology used.

The packet size is not feasible (or is not efficient) for the wireless technology used.

The packet frequency is not feasible (or is not efficient) for the wireless technology used.

Data compression could be used in order to overcome these problems. Yet, if the data to be compressed is real-time data, data compression may not be an option or lead to unsatisfactory results only, because the compression algorithm does not have enough time to gather enough data to perform an efficient compression. Furthermore, data compression being rather CPU-intensive a high energy consumption should be expected. High energy consumption is unwanted in battery-powered devices.

Often the protocol must be modified to be made suitable for the wireless link. This can be done in two ways:

The protocol between sender and receiver is modified. In this way the radio modules of sender and receiver can blindly forward the packets they receive over the serial line.

The protocol between sender and receiver is not modified. However the radio modules of sender and receiver need to implement a modification of the original protocol to talk to each other. Since sender and receiver are unmodified, their respective radio modules still have to support the original protocol on the serial line to communicate with them. The wireless modules have then a translating role.

The second option is usually preferred due to several reasons:

It does not require changing the software of sender or receiver (which is sometimes inaccessible).

It is usually much easier and cheaper to carry out device-external modifications (modifications of a medical sensor may require dramatic changes in the architecture of the entire patient monitor and all its subcomponents).

It guarantees that the wired link will continue to work as it did before when the wireless link is replaced back with the original wired link.

Although, in most cases, the option of an unmodified protocol between sender and receiver is the best option, it still has the disadvantage to require the wireless modules to be programmed with the protocols that enable them to talk to each other and to their hosts (the sender or the receiver). This requires access to the software of the wireless modules—which is not always accessible—and has to be done for every new type of device and/or for every new device combination (e.g. for a patient monitor of type A and an SpO2 sensor, for a patient monitor of type B and the same SpO2 sensor, for the patient monitor of type A and an NIBP sensor, etc.). All that caters for high development costs of any wireless system developed on the basis of a wired system.

Note that the roles of sender and receiver may coincide on the same device so that two devices (e.g. sensor and its patient monitor) communicate with each other in a bidirectional fashion. Moreover the communication system may comprise more than two devices (e.g. patient monitor and two different sensors). The problems described above also apply to the latter cases and so does the present invention.

SUMMARY OF THE INVENTION

The invention relates to a wireless device for medical data transmission that comprises a wireless interface, a processor, and a medical equipment interface arranged to provide connection to an item of medical equipment. The processor is arranged to communicate with the medical equipment interface and the wireless interface, and is also arranged to perform a protocol adaptation. The protocol adaptation takes place from a protocol of incoming data received at the medical equipment interface to a protocol of data to be transmitted through the wireless interface, or vice versa. The protocol adaptation comprises individual or combined filtering, gathering, partitioning, prioritizing, or discarding the incoming data. The processor is further arranged to read a configuration file containing an adaptation specification that pertains to the protocol adaptation, and to perform the protocol adaptation in compliance with the adaptation specification.

The wireless device turns a serial-line-based data transmission system into a wireless data transmission system. The present invention is suited for the field of patient monitoring to cost-effectively turn any wired system (consisting of patient monitors, interfacing devices, telemetry devices and others) into a wireless system. A wireless device for medical data transmission is connected to the serial line of every device that participates in the communication thus interrupting the serial line link(s) between two item of medical equipment. The wireless device can be easily reconfigured by means of a configuration file, which contains all the necessary information for the wireless device to effectively communicate over serial line with an item of medical equipment (host device to the wireless device) and wirelessly with its peer module(s). The configuration file dictates the behavior of the wireless device as to how to adapt the original wire-based protocol to the requirements of the wireless system used to communicate with its peer wireless module(s). The protocol adaptation on the wireless device performs for example the following actions on the data of the original wire-based protocol: filtering, gathering, partitioning, discarding and prioritizing. The configuration file is generated tailored to the needs of each item of medical equipment and/or item combination.

With the present invention, neither access to the host device software nor to the wireless device software or firmware is required. This allows for a modular development process (separation of concerns).

The intrinsic software reusability of the wireless device decreases the development cost of the wireless-enabled system. It usually takes less time to generate a configuration file for a wireless device than to (re-)program the wireless device.

The medical equipment interface may be a receptacle for a cable connecting the wireless device to the item of medical equipment. In the alternative, the wireless device may be configured as a stick (similar to a USB stick) that connects to a jack at the item of medical equipment which obviates the need for a cable and facilitates the handling and use of medical equipment. The cable or the jack may be of the RS232, RS422, RS485 types, the USB type, or any other known data communication standard, including proprietary standards of a manufacturer of medical equipment.

The wireless interface may support a communication standard such as ZigBee, Bluetooth, or IEEE 802.11b.

The processor may be a general purpose microprocessor or microcontroller. Alternatively, it may also be a specialized processor implemented as or within an ASIC (Application Specific Integrated Circuit). An ASIC can be tailored to the requirements of the application which helps improving the performance of the processor and to reduce power consumption to name just two important aspects. The development of wireless devices strives for low power consumptions since these devices are often battery powered. Within an ASIC, a dedicated sub-processor may be provided for each of the mentioned data processing tasks, i.e. filtering, gathering, partitioning, discarding and prioritizing. The sub-processor may be partly hard-wired for this task, but may also accept parameters that change the behavior of the hard-wired portion of the sub-processor.

The protocol adaptation is performed on data that is received at either the medical equipment interface or the wireless interface. Data received from an item of medical equipment such as a Pulse Oximeter (SpO2) or a non-invasive blood pressure sensor (NIBP) may contain dispensable data. This may be due to the fact that an existing item of medical equipment produces more data than actually necessary for a meaningful interpretation of the transmitted data. For example, the temperature of a patient may vary slowly so that a change is not noticeable before a couple of minutes. Keeping this in mind, it is not necessary to transmit a temperature value every second, but every 30 seconds or even less often may also be sufficient. Another example is the bandwidth of ECG (electrocardiogram) data. The American Heart Association recommends a bandwidth of 150 Hz for processing ECG related data. Other experts suggest a bandwidth of 250 Hz for pediatric ECG data. According to the Nyquist-Shannon theorem this means that a sample rate of 500 Hz is sufficient for accurate representation of the analogue ECG signal, even that of a child, in a digitized format. Sensors that employ a larger bandwidth sometimes produce data that is dispensable, i.e. that goes beyond the requirements for accurate data transmission. In addition, some data transmission formats are highly repetitive, because they resend data that has not changed since the last emission. In systems that use a cable for data transmission this was a viable approach, if the cable connection supported the transmitted data rate without degradation of data. Since a cable connected a single sensor (or a limited number of sensors) to e.g. a medical monitor, the entire bandwidth that was offered by the cable could be used for data transmission. A cable-based transmission of medical data was sometimes abundant in terms of bandwidth usage. In contrast, a wireless transmission only has a limited bandwidth available, because only a limited frequency range is reserved for data communication. The protocol adaptation employed in this invention reduces the necessary bandwidth by preventing the transmission of irrelevant data. To this end a wireless device that acts as a sender needs to be able to recognize irrelevant data. The wireless device that acts as a receiver needs to be able to reassemble the data received via its wireless interface. The sending and the receiving wireless device need to perform their respective protocol adaptation according to congruent, matching rules. For example, if the sending wireless device cuts certain items of data prior to transmission, the receiving wireless device needs to be able to reconstruct the left out data items. To this end the wireless devices may for example maintain a table of values that are transmitted often or even regularly. In this case the sending wireless device can detect these values and prevent their transmission. Instead, the sending wireless device can send a shorter data item that tells the receiving wireless device to reinsert the appropriate value stored in the table. In the case of a regular transmission the receiving wireless device may insert the value (and consequently also the corresponding data) on its own initiative at the proper position of a data packet.

A configuration file used for specifying the protocol adaptation may contain filtering patterns, storing patterns, assembly patterns and prioritizing patterns. These patterns contain the conditions under which a certain action should be taken and what the action is. The configuration file is read by a program running on the processor. The processor stores the content of the configuration file in various registers and memories. As explained above, protocol adaptation is subject to a number of basic tasks that are valid for a large number of different protocol adaptations. Each basic task can be configured by parameters contained in the configuration file. The basic tasks define what kinds of aspects of protocol adaptation are feasible and supported by a given wireless device. Accordingly, the manufacturer of a wireless device specifies which basic tasks the wireless device should support, but does not limit the wireless device to a specific use. The latter would be the case if the wireless device was provided with a special program for a given protocol adaptation.

The processor may be arranged to perform the protocol adaptation bi-directionally. This assures that for example handshake procedures between two item of medical equipment (e.g. sensor and monitor) are supported by the wireless devices. Furthermore, only one type of wireless device is needed which increases their flexibility and versatility.

The configuration file may describe the protocol adaptation in a declarative way. The term declarative means that the configuration file describes the properties of the protocol adaptation, not single actions. In general, declarative programming expresses relationships between variables in terms of functions or inference rules and the language executor (interpreter or compiler) applies some fixed algorithm to these relations to produce a result.

The configuration file may describe the protocol adaptation by defining at least one mapping between a data pattern at the medical equipment interface and a data pattern at the wireless interface. The mapping may comprise a transformation rule defining a transformation from the data pattern at the medical equipment interface to the data at the wireless interface or vice versa. This allows defining the protocol adaptation by enabling the processor to recognize a certain data pattern and to perform an action on the underlying data (and possibly also on subsequent data).

The configuration file may describe the protocol adaptation by defining minimum requirements for processing payload data pertaining to the item of medical equipment. A configuration file of this type could be used with a wireless device having some added intelligence. This wireless device could decide on its own, how the protocol adaptation is to be performed. In this case a user needs to provide some basic values of the medical application providing and/or consuming the data to be transmitted, such as a required precision of the samples or maximally admissible delay. The properties of the wireless link are known to the wireless device. These properties of the wireless link include maximal data rate, maximal packet size, currently available bandwidth, or current consumption. The wireless device then decides on the basis of the properties of the medical application and of the wireless link which data reduction strategy to employ. The configuration file is used to communicate the properties of the medical application to the wireless device. The medical application often depends on the item of medical equipment that produces and/or consumes payload data. The sending wireless device and the receiving wireless device need to agree on the actual protocol adaptation. Since both wireless devices use the same configuration file (or two corresponding configuration files) and evaluate it in the same manner, the result is the same. Yet in some cases only the sending wireless device may determine the details of the protocol adaptation. The reason is that the sending wireless device receives the payload data at its medical equipment interface and is able to analyze the payload data. The receiving wireless device does not have this opportunity. Therefore it is contemplated to first cause the sending wireless device to establish a protocol adaptation based on the minimum requirements contained in the configuration file, the properties of the wireless link, and an analysis of the payload data (received at the medical equipment interface of the wireless device). As soon as the sending wireless device has established a set of rules by which protocol adaptation will be performed, the sending wireless device sends the set of rules to the receiving wireless device. The receiving wireless device processes the received set of rules in order to determine how to perform the backward protocol adaptation that allows retrieving a faithful reproduction of the payload data.

The processor is further arranged to read the configuration file from the medical device interface or from the wireless interface so that no additional configuration interface is needed. The wireless device could be connected to a general purpose computer or a Personal Digital Assistant (PDA) by means of a cable or by plugging it directly into the general purpose computer or PDA. In the alternative, a general purpose computer or a PDA could also have a wireless interface allowing communication with the wireless device.

The configuration file may be received from a configuration file tool. With a configuration file tool assisting in the generation of configuration files, the complexity is lower than in software development. A configuration file tool may present the different options of protocol adaptation to a user in an organized fashion. It may also present some preset settings that have been tested. It may also offer to choose from several profiles relating to certain sensor types or monitor types or certain combinations of these. The configuration file tool may also perform the analysis and establishment of possible protocol adaptations when the user indicates minimum requirements for the data transmission, only.

The invention also relates to a wireless communication system for medical data transmission comprising a first and a second wireless device that both correspond to the description given above. The first wireless device and the second wireless device communicate through their respective wireless interfaces. In this communication system the sending and the receiving are matched to each other.

The second wireless device may communicate with a plurality of first wireless devices. Some medical data monitors are capable of displaying several measurements at once so that it is possible to group the receiving wireless devices in a single wireless device.

The present invention also relates to a method for setting up a first wireless device, the first wireless device being arranged to communicate with an item of medical equipment via a corresponding medical equipment interface of the first wireless device, to communicate with a second wireless device via a wireless communication path and a corresponding wireless interface of the first wireless device; and to perform a protocol adaptation between data received from the item of medical equipment and data to be transmitted to the second wireless device (and vice versa). The protocol adaptation comprises individual or combined filtering, gathering, partitioning, prioritizing, or discarding the incoming data. The method comprises:
running a generic operating program on the first wireless device;
causing the generic program to read a configuration file;
analyzing a content of the configuration file; and
storing the content in a memory of the first wireless device, the memory being arranged to be consulted during a definition of the protocol adaptation.

The combination of a generic operating program and a configuration file adds to the flexibility of the wireless devices. Setting up or configuring a wireless device for a specific medical application with the present invention is easy for a user to accomplish and does not require programming skills. The hardware including medical sensors, medical monitors and the wireless devices remain basically unchanged. There is no need to change for example the protocol of a medical sensor in order to match the capabilities of the wireless devices. Only the configuration file is changed when the wireless device is used with different items of medical equipment. Configuration files may be provided by the manufacturer of the wireless device for common medical equipment. On the other hand, if a new item of medical equipment is marketed, the manufacturer of the newly marketed item may provide a suitable configuration file together with the item. Wireless links between a medical sensor and a medical monitor are likely to become more and more popular. Therefore medical equipment manufacturers might be able to boost their sales, if their products support a compatibility with a wireless data transmission system as described herein.

The configuration file may describe the protocol adaptation in a declarative way.

The configuration file may describe the protocol adaptation by defining at least one mapping between a data pattern at the medical equipment interface and a data pattern at the wireless interface. The mapping may comprise a transformation rule defining a transformation from the data pattern at the medical equipment interface to the data at the wireless interface or vice versa.

The configuration file may describe the protocol adaptation by defining minimum requirements for processing payload data pertaining to the item of medical equipment.

The configuration file may be read from the medical device interface or from the wireless interface.

The configuration file may be received from a configuration file tool.

DETAILED DESCRIPTION OF THE PRESENT INVENTION

Figure 1:
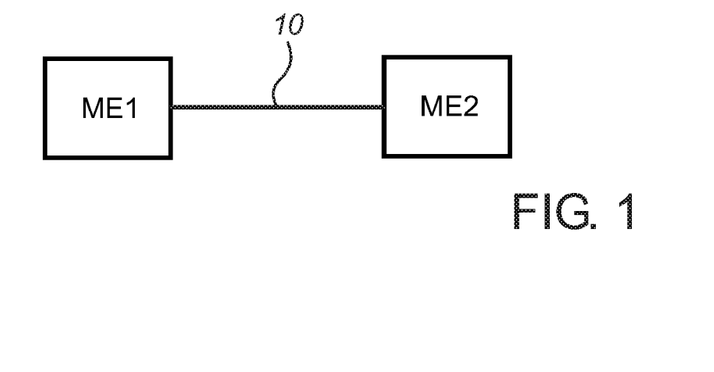
FIG. 1 is a schematic representation of the prior art.

FIG. 1 depicts a wire-based system of the prior art. A first item of medical equipment ME1 is connected to a second item of medical equipment ME2 via a cable-based link 10. The first item of medical equipment is for example a medical sensor for non-invasive blood pressure measurement (NIBP) or a Pulse Oximeter (SpO2). The second item of medical equipment is for example a medical monitor for displaying the data acquired by the first item of medical equipment.

Figure 2:
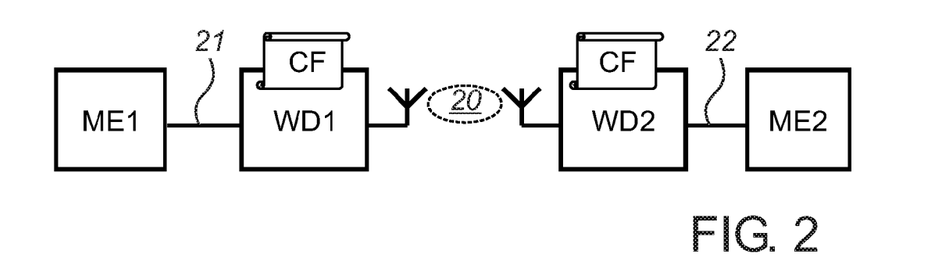
FIG. 2 is a schematic representation of a wireless data transmission system having to wireless devices according to the present invention.

FIG. 2 illustrates the application of the invention to the system of FIG. 1. The new wireless system consists of the two original items of medical equipments ME1, ME2 (also called host devices) and two wireless devices for medical measurements WD1, WD2. The items of medical equipment ME1, ME2 communicate with their respective wireless devices WD1, WD2 via connections 21 and 22, respectively. The two wireless devices WD1 and WD2 communicate with each other via a wireless link 20. Each wireless device WD1, WD2 is provided a configuration file CF that specifies the actions to be taken on the input data for the wireless device. The wireless device WD1, WD2 may receive input data at a medical equipment interface of the wireless device or at a wireless interface of the wireless device. In case the wireless device WD1, WD2 is arranged for bi-directional transmission, it is able to accept input data at both of its interfaces and pass it on to the respective other interface after suitable data processing in accordance with the configuration file.

A configuration file may contain the following information for each interface:
- connection settings (language to speak with the host device or with another wireless device)
- serial line (if the interface is wired)
- baud rate
- parity
- data bits
- stop bits
- direction of data
- flow control
- wireless settings (if the interface is wireless-optional)
- input frame structure (point of reference that allow the wireless device to find data in the input stream)
- start of frame code (if any)
- list of possible header codes (if any)
- position of length field in the frame (if any)
- length of frame
- end-of-frame (EOF) code (if any)
- output frame structure (structure of the frame to be generated by the wireless device)
- start of frame code (if any)
- list of possible header codes (if any)
- position of length field in the frame (if any)
- length of frame (if it is fixed)
- end-of-frame (EOF) code (if any)
- filtering pattern (redundant or irrelevant information to be scrapped from the input data stream)
- condition (may be based on flags in the packet header)
- first byte
- last byte
- storing pattern (information of interest to be stored for later transmission)
- condition (may be based on flags in the packet header)
- first byte
- last byte
- identifier of stored data
- assembly pattern (how to assemble the received information in a new data frame)
- condition to pack new frame (optional)
- amount of stored data to be packed (optional)
- list of data identifiers to be packed (optional)
- prioritizing pattern
- condition (may be based on flags in the packet header or a given code found in the input format)
- format of priority data input frame The XML format appears to be suitable as format for a configuration file. The XML format is cited as one possible example that does not exclude other suitable formats. The XML format offers the option of hierarchically organizing the content of the file. A number of well tested tools for editing, checking and evaluating XML-files exist.

Figure 3:
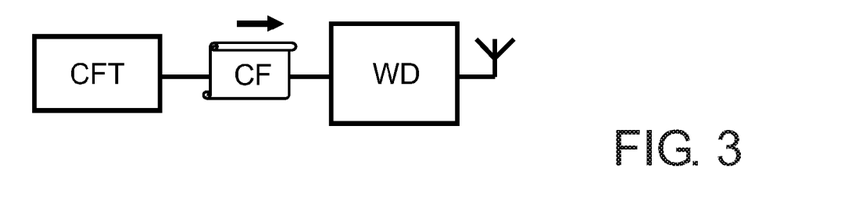
FIG. 3 is a schematic representation of a first option of configuring a wireless device.
Figure 4:
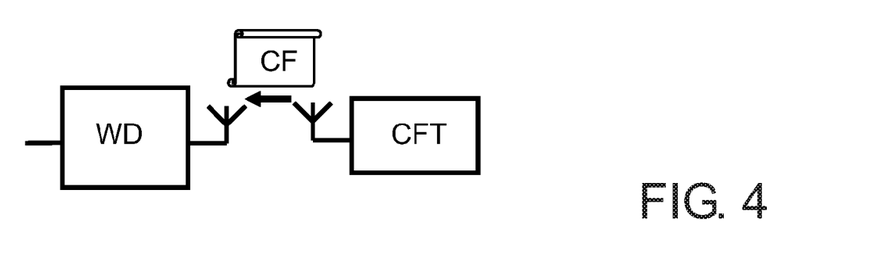
FIG. 4 is a schematic representation of a second option of configuring a wireless device.

FIGS. 3 and 4 show how the configuration file may be loaded into the wireless device. A first option is to provide a dedicated configuration interface. In the alternative the configuration file may also be loaded over the medical equipment interface before the wireless device is connected to its host device (FIG. 3), or over the wireless interface (FIG. 4), either before or after the wireless device is connected to its host device. A special reset command sets the wireless device in a configuration state, in which it waits for the reception of the configuration file. The configuration file is generated and sent to the wireless device by a configuration file tool, which can be a PC, a PDA, or any other electronic device that has at least one compatible interface with the wireless device.

Figure 5:
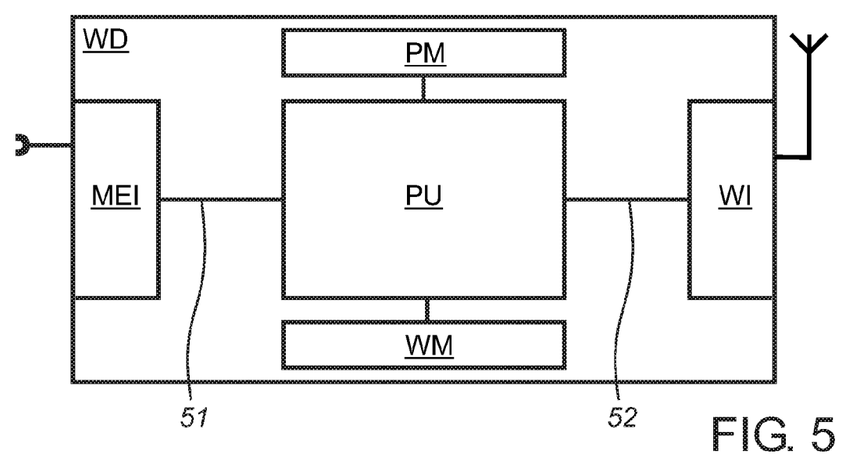
FIG. 5 is a schematic representation of a wireless device.

FIG. 5 illustrates a possible schematic structure of a wireless device WD according to the present invention. The wireless device WD comprises a medical equipment interface MEI that provides connection to an item of medical equipment. The medical equipment interface as presented in FIG. 5 provides a jack for connecting a cable that leads to the item of medical equipment. Inside the wireless device WD the medical equipment interface is connected to a processor (processing unit) PU via a connection 51. The processor PU performs the actual protocol adaptation. It is connected to a working memory WM and a parameter memory PM. The working memory WM and the parameter memory PM could also be combined. Data that was received at one interface, i.e. medical equipment interface or wireless interface can be temporarily stored in the working memory WM. This may be useful if certain parts of the received data need not be transmitted immediately or if they can be used as reference data for subsequent transmissions or data processing routines. The parameter memory stores parameter values that relate to the current protocol adaptation scheme. The parameter memory is populated during the set up (configuration) of the wireless device with parameter values that are read from one or several configuration files. The processor is also connected to a wireless interface WI via a connection 52. The wireless interface is further connected to an antenna for sending and/or receiving wireless data.

Figure 6:
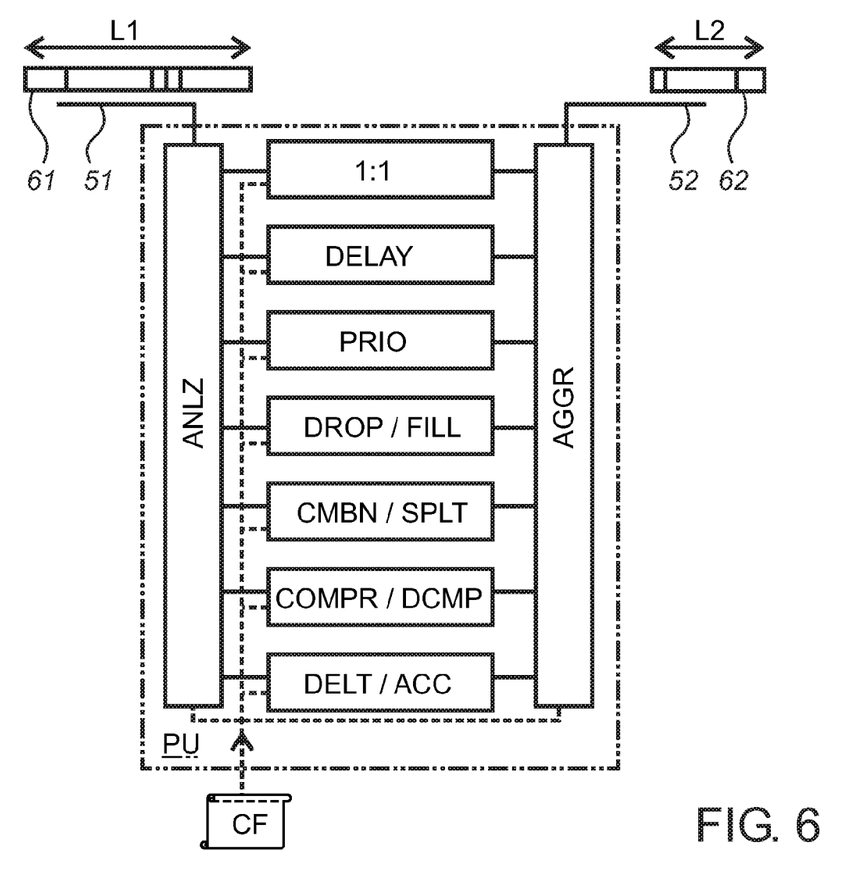
FIG. 6 is a schematic representation of a processor of a wireless device.

FIG. 6 shows a schematic illustration of the processor PU of a bi-directional wireless device WD. The processor PU receives a frame of data 61 on connection 51 (FIG. 5). The data frame 61 has a length L1. The data frame 61 is first directed to an analyzer ANLZ. The analyzer ANLZ determines sections within the data frame 61 that indicate a possible data reduction. In particular, the analyzer ANLZ seeks flags within the data frame 61 that precede irrelevant data. Irrelevant data could be for example the repetitive transmission of an identification number of the item of medical equipment. It would be sufficient to send the identification number once at the beginning of the transmission. The analyzer ANLZ could also look out for data that is identical to preceding data. Depending on the data the analyzer ANLZ finds in data frame 61, it determines which action should be taken in order to perform the desired protocol adaptation. In most applications, reducing the required bandwidth is an important goal of protocol adaptation. However, a protocol adaptation could also be used for other reasons such as increasing the robustness of the transmitted data towards interferences. If the analyzer ANLZ has decided which action should be taken on the current data, it directs the concerned portion of data frame 61 to one of several processing modules. The exemplary processing modules shown in FIG. 6 are:

- 1:1 performs a 1-to-1 operation, i.e. an identity operation
- DELAY performs a delay on data that do not require immediate transmission
- PRIO performs a priority operation so that presented data is transmitted as soon as possible
- DROP/FILL performs dropping of data and complementary filling of data
- CMBN/SPLT performs combining of data and complementary splitting of data
- COMPR/DCMP performs compression and decompression
- DELT/ACC performs evaluation of data variations (Δ data) and complementary accumulation.

The modules could be hardwired, implemented in software, or partly implemented in hardware and partly in software.

The 1:1-module (or identity module) is used, if no protocol adaptation is possible. This may be the case if the data for transmission cannot be compressed or reduced further.

The DELAY module may be used if the transmission of a part of data can be postponed. This applies for example to data representing cumulated reports or statistics that a user, such as a nurse or a physician, evaluates later, anyway. Accordingly, transmission of this data could be triggered when the user attempts to retrieve the data. In the alternative, the transmission takes place when the wireless link is relatively idle.

The PRIO module places data at the top of a waiting queue for transmission if the priority of the data is high so that fast transmission is required. Data that is highly prioritized could be an alarm such as overstepping of threshold values for the measured variable, or a low battery alarm at one of the items of medical equipment or the wireless devices.

The DROP/FILL module relates to data that needs not to be transmitted because it is redundant or irrelevant. At the sender side the module acts as module that drops this kind of data. At the receiver side, the data must be refilled into the data frame by the receiving wireless device in order to create a close reproduction of the original data frame. The receiving wireless device either knows which values to insert from the configuration or file, or the sending wireless device informs the receiving wireless device about the values to fill in during an initial transmission. The sending wireless device may also send a schedule defining the times or conditions of the refilling action. Yet another alternative is to send a flag that instructs the FILL module at the receiver side to insert a certain data value. The FILL module may also be regarded as a repeat module at the receiving side that repeats certain data values according to the schedule.

The CMBN/SPLT (combine/split) module can be used for example on data that contains several channels, such as from different ECG electrodes. Instead of transmitting each channel separately the channels can be combined. Even if the signals on the different channels are not identical, they are at least usually similar. Accordingly a combined signal may be created by the sending CMBN module in which the signal of one main channel is represented along with the differences of the other channels to the main channel signal. The difference signals may have less resolution than the original channels resulting in an economy of bandwidth. At the receiver side, the combined signal that is transmitted via the wireless link has to be split up into separate signals again.

The COMPR/DCMP module is for compressing and decompressing data prior to transmission via the wireless link. The compression of data is an option when data reduction cannot be achieved by means of an explicit rule. At the receiver side decompression is performed.

The DELT/ACC module can be used on data that varies relatively slowly. At the sender side the module transmits the difference or variation of a value with respect to a preceding value. At the receiving side the original signal is restored again by accumulating the variations. Of course, sending the full value from time to time is advisable in order to prevent a slow deviation from the true values.

The processor PU also has an aggregator AGGR that builds a data frame 62 for transmission over the wireless link. The data frame 62 is build from the data that the different modules provide. The data frame 62 is send to the wireless interface WI (FIG. 5) via connection 52.

In the case of a bi-directional wireless device, the analyzer ANLZ and the aggregator AGGR are interchangeable. Thus, line 51 could be connected to the aggregator AGGR, and line 52 could be connected to the analyzer ANLZ. The aggregator AGGR could also assume the role of the analyzer ANLZ and vice versa.

When comparing the length L1 of data frame 61 to the length L2 of data frame 62, it can be observed that a significant reduction of data is normally achieved.

The configuration file is read and evaluated during the set up of the wireless device. The set up procedure is initiated by a special reset command. The values of different parameters that are contained in the configuration file are distributed to the analyzer ANLZ, the aggregator AGGR, and to the different modules as indicated by dotted lines in FIG. 6. In the alternative the values can be stored to the parameter memory PM (FIG. 5). In operation any intermediate results that need to be stored for a period of time may be stored to the working memory WM (FIG. 5). As an example, an intermediate result could be the last value of a signal in the context of the DELT/ACC module which is needed in order to calculate the difference of the current value with respect to that last value. The intermediate results could also be stored in dedicated registers of the processor which shortens access time compared to retrieving the value from the working memory.

The invention claimed is:

1. A wireless communication system for wireless medical data transmission between first and second items of medical equipment which are configured to communicate with each other non-wirelessly with a first communication protocol, the system comprising:

a first wireless device including:
  a first medical equipment interface arranged to provide connection to the first item of medical equipment;
  a first wireless interface;
  one or more first processors programmed to perform a protocol adaptation from at least one of:
    the first communications protocol of incoming data received at the first medical equipment interface to a second communications protocol of data to be wirelessly transmitted by said first wireless interface, and,
    the second communications protocol of incoming data received at the first wireless interface and the first communications protocol of data to be transmitted through the first medical equipment interface to the first item of medical equipment; and,
a second wireless device including:
  a second medical equipment interface arranged to provide connection to the second item of medical equipment;
  a second wireless interface which wirelessly communications with the first wireless interface using the second communications protocol;
  one or more second processors programmed to perform a protocol adaptation from at least one of:
    the second communication protocol of incoming data received at the second wireless interface and the first communication protocol of data to be transmitted through the second medical equipment interface,
    the first communication protocol of incoming data received at the second medical equipment interface to the second communication protocol of data to be transmitted through said second wireless interface, and,
    said protocol adaptations comprising individual or combined filtering, gathering, partitioning, prioritizing, or discarding said incoming data;
wherein said first wireless device and said second wireless device communicate through their respective wireless interfaces;
wherein the first and second wireless devices further include:
  first and second parameter memories configured to store a configuration file containing an adaptation specification pertaining to the protocol adaptation;
wherein said one or more first and second processors are further programmed to:
  in a configuration state, receive the configuration file via one of the medical equipment interface and the wireless interface and load the configuration file in the parameter memory;
  read the configuration file containing the adaptation specification that pertains to said protocol adaptation; and
  perform said protocol adaptation in compliance with said adaptation specification;
wherein said configuration file describes said protocol adaptation by defining at least one mapping between a data pattern at said medical equipment interfaces and a data pattern at said wireless interfaces, said mapping comprising a transformation rule defining a transformation from said data pattern at said medical equipment interfaces to said data at said wireless interfaces or vice versa.

2. Wireless communication system for wireless medical data transmission between first and second items of medical equipment which are configured to communicate with each other non-wirelessly with a first communication protocol, the system comprising:
  a first wireless device including:
    a first medical equipment interface arranged to provide connection to the first item of medical equipment;
    a first wireless interface;
    one or more first processors programmed to perform a protocol adaptation from at least one of:
      the first communications protocol of incoming data received at the first medical equipment interface to a second communications protocol of data to be wirelessly transmitted by said first wireless interface, and,
      the second communications protocol of incoming data received at the first wireless interface and the first communications protocol of data to be transmitted through the first medical equipment interface to the first item of medical equipment; and,
  a second wireless device including:
    a second medical equipment interface arranged to provide connection to the second item of medical equipment;
    a second wireless interface which wirelessly communications with the first wireless interface using the second communications protocol;
    one or more second processors programmed to perform a protocol adaptation from at least one of:
      the second communication protocol of incoming data received at the second wireless interface and the first communication protocol of data to be transmitted through the second medical equipment interface,
      the first communication protocol of incoming data received at the second medical equipment interface to the second communication protocol of data to be transmitted through said second wireless interface, and,
      said protocol adaptations comprising individual or combined filtering, gathering, partitioning, prioritizing, or discarding said incoming data;
wherein said first wireless device and said second wireless device communicate through their respective wireless interfaces
wherein the first and second wireless devices further include:
  first and second parameter memories configured to store a configuration file containing an adaptation specification pertaining to the protocol adaptation;
wherein said one or more first and second processors are further programmed to:
  in a configuration state, receive the configuration file via one of the medical equipment interface and the wireless interface and load the configuration file in the parameter memory;
  read the configuration file containing the adaptation specification that pertains to said protocol adaptation; and
  perform said protocol adaptation in compliance with said adaptation specification;
wherein said one or more first processors are further programmed to:
  analyze data frames of the incoming data received on the first medical equipment interface for sections that indicate a possible data reduction to reduce bandwidth; and reduce bandwidth by:
delaying transmission of low priority data,
determining high priority data and expediting transmission of the high priority data,
dropping irrelevant and redundant data,
combining similar data,
compressing data, and
transmitting a difference or variation with respect to a preceding value of the received data.

3. A wireless communication system for wireless medical data transmission between first and second items of medical equipment which are configured to communicate with each other non-wirelessly with a first communication protocol, the system comprising:
a first wireless device including:
a first medical equipment interface arranged to provide connection to the first item of medical equipment;
a first wireless interface;
one or more first processors programmed to perform a protocol adaptation from at least one of:
the first communications protocol of incoming data received at the first medical equipment interface to a second communications protocol of data to be wirelessly transmitted by said first wireless interface, and,
the second communications protocol of incoming data received at the first wireless interface and the first communications protocol of data to be transmitted through the first medical equipment interface to the first item of medical equipment; and,
a second wireless device including:
a second medical equipment interface arranged to provide connection to the second item of medical equipment;
a second wireless interface which wirelessly communications with the first wireless interface using the second communications protocol;
one or more second processors programmed to perform a protocol adaptation from at least one of:
the second communication protocol of incoming data received at the second wireless interface and the first communication protocol of data to be transmitted through the second medical equipment interface,
the first communication protocol of incoming data received at the second medical equipment interface to the second communication protocol of data to be transmitted through said second wireless interface, and,
said protocol adaptations comprising individual or combined filtering, gathering, partitioning, prioritizing, or discarding said incoming data
wherein said first wireless device and said second wireless device communicate through their respective wireless interfaces;
wherein the one or more first and second processors are further programmed to:
run a generic operating program on said first and second wireless devices;
cause said generic program to read a configuration file from the first and/or second item of medical equipment;
analyze a content of said configuration file;
store said content in first and second memories of the first and second wireless devices, said memory being arranged to be consulted during a definition of said protocol adaptation;
wherein said configuration file describes said protocol adaptation by defining at least one mapping between a data pattern at said medical equipment interfaces and a data pattern at said wireless interfaces, said mapping comprising a transformation rule defining a transformation from said data pattern at said medical equipment interfaces to said data at said wireless interfaces or vice versa.

4. A wireless communication system for wireless medical data transmission between first and second items of medical equipment which are configured to communicate with each other non-wirelessly with a first communication protocol, the system comprising:
a first wireless device including:
a first medical equipment interface arranged to provide connection to the first item of medical equipment;
a first wireless interface;
one or more first processors programmed to perform a protocol adaptation from at least one of:
the first communications protocol of incoming data received at the first medical equipment interface to a second communications protocol of data to be wirelessly transmitted by said first wireless interface, and,
the second communications protocol of incoming data received at the first wireless interface and the first communications protocol of data to be transmitted through the first medical equipment interface to the first item of medical equipment; and,
a second wireless device including:
a second medical equipment interface arranged to provide connection to the second item of medical equipment;
a second wireless interface which wirelessly communications with the first wireless interface using the second communications protocol;
one or more second processors programmed to perform a protocol adaptation from at least one of:
the second communication protocol of incoming data received at the second wireless interface and the first communication protocol of data to be transmitted through the second medical equipment interface,
the first communication protocol of incoming data received at the second medical equipment interface to the second communication protocol of data to be transmitted through said second wireless interface, and,
said protocol adaptations comprising individual or combined filtering, gathering, partitioning, prioritizing, or discarding said incoming data;
wherein said first wireless device and said second wireless device communicate through their respective wireless interfaces;
wherein the first item of medical equipment generates data frames in a first medical equipment format;
wherein the one or more first processors are further programmed to:
receive a configuration file which specifies a protocol for analyzing and reconfiguring first medical equipment format data frames received from the first item of medical equipment into a shortened format for wireless transmission;
store the configuration file protocol in a first wireless device memory,
receive the first medical equipment format data frames from the first medical equipment interface, analyze and reconfigure the first received medical equipment format data frames in accordance with the configuration file protocol stored in the first wireless device memory into the shortened format data frames, and control the first wireless interface to wirelessly transmit the shortened format data frames;

wherein the second wireless device includes a second memory, the one or more second processors being programmed to:

receive the configuration file which specifies the protocol for analyzing and reconfiguring the shortened format data frames received from the second wireless interface into a second item of medical equipment format;

store the configuration file protocol in the second memory, receive the shortened format data frames from the second wireless interface, analyze and reconfigure the received shortened format data frames in accordance with the configuration file protocol into the second item of medical equipment format, and control the second medical device interface to send the second item of medical equipment format data frames to the second item of medical equipment via the second medical device interface; and wherein the one or more first processors are further programmed to:

analyze data frames of the incoming data for sections that indicate a possible data reduction to reduce bandwidth; and reduce bandwidth by:
    delaying transmission of low priority data,
    determining high priority data and expediting transmission of the high priority data,
    dropping irrelevant and redundant data,
    combining similar data,
    compressing data, and
    transmitting a difference or variation with respect to a preceding value of the received data.

5. The wireless communication system of claim 4 wherein the second processor is further programmed to:

refill the shortened format data frames to reproduce the first item of medical equipment data frames;

split the combined similar data into different channels;

decompress the compressed data;

restore the preceding values by accumulating the differences or variations.

\* \* \* \* \*